United States Patent [19]

Grunchard et al.

[11] Patent Number: 5,714,652
[45] Date of Patent: Feb. 3, 1998

[54] PROCESS FOR THE PREPARATION OF 1,1-DIFLUOROETHANE

[75] Inventors: Frans Grunchard, Ixelles; Francine Janssens, Vilvoorde; Vincent Wilmet, Wavre, all of Belgium

[73] Assignee: Solvay (Société Anonyme), Brussels, Belgium

[21] Appl. No.: 630,173

[22] Filed: Apr. 11, 1996

[30] Foreign Application Priority Data

Apr. 24, 1995 [FR] France ..................... 95.04962

[51] Int. Cl.$^6$ ........................................ C07C 17/00
[52] U.S. Cl. ...................... 570/165; 570/167; 570/164
[58] Field of Search ............................ 570/164, 165, 570/167

[56] References Cited

FOREIGN PATENT DOCUMENTS

| 600536 | 8/1994 | European Pat. Off. . |
| 0637579A1 | 2/1995 | European Pat. Off. . |

OTHER PUBLICATIONS

CA 95:62770 (1981).

Primary Examiner—Paul J. Killos
Attorney, Agent, or Firm—Spencer & Frank

[57] ABSTRACT

The invention relates to a process for the preparation of 1,1-difluoroethane by reaction of vinyl chloride with hydrogen fluoride, in the presence of perchloroethylene or 1,1,1,3,3-pentafluorobutane.

11 Claims, No Drawings

PROCESS FOR THE PREPARATION OF 1,1-DIFLUOROETHANE

The present invention relates to a process for the preparation of 1,1-difluoroethane starting from vinyl chloride, performed in the liquid phase.

Patent application EP-A-0,637,579 discloses a process for the production of 1,1-difluoroethane by reaction between vinyl chloride and hydrogen fluoride in the liquid phase in the presence of a hydrofluorination catalyst and a saturated halogen-containing hydrocarbon, 1,2-dichloroethane, 1,2,3-trichloropropane, 1-chloro-1-fluoroethane, 1,1-difluoroethane, 1,1-dichloroethane and 1,3-dichloro-1-fluorobutane and mixtures thereof being preferred.

In this known process, some of the vinyl chloride is converted into heavy halogen-containing side products, whose accumulation causes a progressive deactivation of the catalyst over time. In addition, the reaction products leaving the reactor are inevitably contaminated with vinyl choride, in an amount such that its removal may prove to be difficult.

The aim of the present invention is to improve the abovementioned known process, so as to overcome the deactivation of the catalyst and to decrease the content of residual vinyl chloride in the reaction products.

Consequently, the invention relates to a process for the manufacture of 1,1-difluoroethane by reaction between hydrogen fluoride and vinyl chloride in the liquid phase, which is characterized in that the reaction is carried out in a reaction medium comprising at least one compound chosen from perchloroethylene and 1,1,1,3,3-pentafluorobutane. Perchloroethylene is preferred.

The term reaction medium is understood to denote all of the liquid medium formed of the abovementioned compound, the hydrogen fluoride and the vinyl chloride used, products formed by the reaction of the hydrogen fluoride and the vinyl chloride and, where appropriate, other additives usually used in processes for the fluorination of halogen-containing hydrocarbons, such as catalysts.

In the process according to the invention, the reaction medium usually contains at least 20% by weight of the abovementioned compound. Preferably, the reaction medium contains at least 30% by weight thereof. In a particularly preferred manner, it contains at least 40% by weight thereof. The best results are obtained with a content of abovementioned compound in the reaction medium of greater than or equal to 45% by weight. In general, the reaction medium contains a maximum of 99.5% by weight of the abovementioned compound. Preferably, it contains not more than 98.5% thereof. In a particularly preferred manner, it contains not more than 95% thereof. Very good results have been obtained with a content of abovementioned compound in the reaction medium of less than or equal to 90%.

The reaction medium usually contains at least 0.2% by weight of hydrogen fluoride. Preferably, the reaction medium contains at least 1% by weight of hydrogen fluoride. In a particularly preferred manner, it contains at least 5% by weight thereof. The best results are obtained with a content of hydrogen fluoride in the reaction medium of greater than or equal to 10% by weight. In general, the content of hydrogen fluoride in the reaction medium is not more than 75% by weight. Preferably, it is less than or equal to 60%. Very good results have been obtained with a content of hydrogen fluoride in the reaction medium not exceeding 50% by weight. A content of hydrogen fluoride in the reaction medium of from 15 to 40% is most particularly advantageous.

The lower the content of vinyl chloride in the reaction medium, the lesser is the formation of heavy side products. The reactivity of the vinyl chloride and of the hydrogen fluoride in the reaction medium is such that it is possible to work with a content of vinyl chloride in the reaction medium of about 0.003% by weight. In practice, it is preferable to work with a content of vinyl chloride in the reaction medium of at least 0.005% by weight. A content of vinyl chloride of at least 0.01% by weight is particularly preferred. Very good results have been obtained with a content of vinyl chloride of about 0.03% by weight. The process is generally performed with a content of vinylchloride of less than 15% of the weight of the reaction medium. Advantageously, the process is performed with a content of vinyl chloride of less than 10% by weight. In a particularly advantageous manner, it does not exceed 5% by weight at any given moment. In a most particularly advantageous manner, the process is performed with a content of vinyl chloride of less than 2% by weight.

The reaction medium may also contain various additives, in particular a hydrofluorination catalyst. The presence of a catalyst is desirable in order to obtain the 1,1-difluoroethane under industrially exploitable conditions. As catalysts which may be used, mention may be made of metal derivatives chosen from the metals of groups IIIa, IVa, IVb, Va, Vb and VIb of the Periodic Table of the Elements, and mixtures thereof. Derivatives of titanium, vanadium, tantalum, molybdenum, tungsten, tin and antimony are more especially selected. The tin, titanium, molybdenum and tungsten derivatives are preferred. The tin derivatives are particularly suitable. Metal derivatives which are preferably used are halides, such as the chlorides, fluorides and chlorofluorides, as well as oxides and oxyhalides. Catalysts particularly preferred for preparing 1,1-difluoroethane by the process according to the present invention are tin chloride, fluoride and chlorofluoride. The use of $SnCl_4$ in the process according to the invention is particularly advantageous. As a function of the reaction conditions, the latter may be at least partially fluorinated in situ.

The amount of catalyst used may vary within a wide range. Usually, the catalyst is used in a proportion of 0.001 to 2 mol of catalyst per kg of reaction medium, and preferably of 0.01 to 1 mol per kg.

When the abovementioned compound is 1,1,1,3,3-pentafluorobutane, a one-phase reaction medium is generally obtained. When the abovementioned compound is perchloroethylene, a two-phase reaction medium is usually obtained, consisting of a heavy phase rich in organic compounds and a light phase rich in hydrogen fluoride.

The process according to the invention may be performed in a batchwise or continuous manner. An advantageous embodiment of the process consists in introducing the vinyl chloride and the hydrogen fluoride reactants continuously into the reactor containing the said compound and, optionally, an excess of hydrogen fluoride and a catalyst and in withdrawing the 1,1-difluoroethane continuously from the reaction medium.

In the process according to the invention, the hydrogen fluoride is advantageously introduced in a hydrogen fluoride/vinyl chloride molar ratio which is at least 2. Usually, this molar ratio does not exceed 20. Preferably, it does not exceed 5. Excellent results have been obtained with a molar ratio of 2 or slightly above, for example from 2.05 to 2.5.

In the process according to the invention, the hydrogen fluoride and the vinyl chloride may be introduced into the reaction medium either in the liquid state or in the vapour state. On account of the presence of the abovementioned compound, the vinyl chloride may even be introduced into the reactor in the liquid state without causing the formation of large amounts of heavy side products.

The duration of the reaction required to ensure an optimum yield of 1,1-difluoroethane varies according to the operating conditions and, in practice, may readily be evaluated experimentally. When the process is carried out continuously, the conventional residency time, that is to say the ratio between the volume of the reaction medium contained in the reactor and the total flow rate of vinyl chloride and hydrogen fluoride in the liquid state is generally from 0.1 to 5 hours.

The process according to the invention may be performed within a wide range of temperatures and pressures, in which the reaction medium is liquid. Generally, the temperature at which the reaction is performed is at least 40° C. and does not exceed 130° C. Preferably, it is at least 50° C. and does not exceed 120° C. Generally, the process is performed with a pressure of at least about 2 bar. A pressure of at least about 5 bar is preferred. A pressure of at least about 8 bar is particularly preferred. Usually, this pressure does not exceed about 50 bar, pressures of less than or equal to about 30 bar being especially recommended.

According to a particularly preferred embodiment of the invention, the reaction temperature and pressure are regulated so as, on the one hand, to ensure the maintenance of the reaction medium in the liquid phase and, on the other hand, to allow the 1,1-difluoroethane and the co-produced hydrogen chloride to leave the reaction medium in gaseous form. To do this, the process is generally performed at temperatures of between 60° and 120° C. and at pressures of between 2 and 30 bar. Temperatures of between 70° and 100° C. and pressures of between 7 and 15 bar have proven to be advantageous.

In this particularly preferred embodiment of the invention, the gaseous medium which is collected contains, besides the 1,1-difluoroethane and hydrogen chloride, a little hydrogenfluoride, optionally a little 1-chloro-1-fluoroethane produced by incomplete fluorination of the vinyl chloride, and, optionally, a little of the abovementioned compound. Typically, it contains not more than 100 ppm of vinyl chloride. When the reaction medium contains perchloroethylene, a content of vinyl chloride not exceeding 30 ppm may even be obtained. The gaseous medium may be subjected to one or more separation steps by techniques which are known per se, so as to collect the 1,1-difluoroethane in substantially pure form. The hydrogen chloride, the hydrogen fluoride and the abovementioned compound may be separated, for example by distillation. At the low concentrations obtained by the process according to the invention, the residual vinyl chloride may readily be removed by absorption onto active charcoal.

The process according to the invention may be carried out in any type of reactor or equipment which allows the conditions described to be united and in particular to be pressure-resistant and resistant to hydrogen fluoride. Usually, the process according to the invention is performed in a reactor equipped with a device for withdrawing a stream of gas, for example in a reactor over which is mounted a column and a reflux condenser. This device makes it possible, by suitable adjustment, to withdraw the 1,1-difluoroethane and the hydrogen chloride produced in the gaseous phase, while at the same time keeping the other constituents of the reaction medium in the reactor.

The process according to the invention has certain appreciable advantages relative to the process described in patent application EP-A-0,637,579. It makes it possible in particular to obtain 1,1-difluoroethane with a selectivity and a yield which are considerably greater than those obtained in the known processes. In particular, it generates far fewer heavy side products and very markedly improves the stability of the catalyst, thereby dispensing with the need for frequent purging of a fraction of the reaction medium and introduction of fresh catalyst. Furthermore, the considerable increase in reactivity of the vinyl chloride towards hydrogen fluoride observed in the process according to the invention imparts to the process a productivity which is largely superior to that of the known processes and also makes it possible to obtain directly a gaseous mixture at the reactor outlet typically containing only from 10 to 100 ppm of vinyl chloride, thereby avoiding difficult and expensive treatments for the purification of the 1,1-difluoroethane.

As a variant, in the process according to the invention, the vinyl chloride may be replaced by 1,1-dichloroethane or 1-chloro-1-fluoroethane.

The examples below illustrate the invention in a non-limiting manner.

EXAMPLE I (COMPARISON)

Into a 0.5 l autoclave made of Hastelloy® B2 alloy, equipped with a paddle stirrer and over which is mounted a jacketed condenser, placed under vacuum beforehand, were introduced at room temperature 108 g of 1,1-difluoroethane, in accordance with the process described in application EP-A-0,637,579, 15 g of $SnCl_4$ and 135 g of hydrogen fluoride. The autoclave was then immersed in a thermostatically regulated oil bath and heated until a temperature of 85° to 90° C. was obtained. The pressure in the autoclave and the condenser was adjusted to 12 bar. The autoclave was then supplied continuously with hydrogen fluoride and vinyl chloride, at a vinyl chloride flow rate of 15 g/h and a hydrogen fluoride/vinyl chloride molar ratio of 2. The condenser was maintained at a temperature of 30° C., the condensate being sent continuously to the autoclave and the gaseous effluents neutralized in a scrubber using concentrated potassium hydroxide solution. The reaction was monitored on the basis of the analysis of samples taken regularly from the liquid medium in the autoclave, analysis of the composition of the gaseous effluents exiting the scrubber and analysis of the chlorides and fluorides collected from the scrubber.

The most significant results are presented in the single table. These are the duration of the reaction before observation of a decrease in the catalytic activity, the proportion by weight of heavy side products formed relative to the vinyl chloride (VC) converted (selectivity towards heavy side products) and the minimum content of vinyl chloride observed in the gaseous effluents ($[VC]_{min}$). The decrease in catalytic activity is marked by a decrease in the productivity of 1,1-difluoroethane, coinciding with an increase in the concentration of vinyl chloride in the gaseous effluents and an accumulation of 1-chloro-1-fluoroethane and 1,1-dichloroethane in the reaction medium.

EXAMPLE 2 (COMPARISON)

The test of Example 1 was repeated, replacing the 1,1-difluoroethane with 1,2,3 - trichloropropane. The pressure was adjusted to 10 bar. The results are shown in the single table.

EXAMPLES 3 AND 4 (ACCORDING TO THE INVENTION)

The test of Example 1 was repeated, replacing the 1,1-difluoroethane by 1,1,1,3,3-pentafluorobutane (Example 3;

pressure adjusted to 12 bar) or perchloroethylene (Example 4; pressure adjusted to 10 bar). The results are also given in the single table.

Analysis of the table reveals the progress achieved by incorporating 1,1,1,3,3-pentafluorobutane or perchloroethylene into the reaction medium, in accordance with the invention. This progress is manifested by a marked increase in the lifetime of the catalyst and by a significant decrease in the amount of heavy side products formed and the residual content of vinyl chloride in the reaction products.

TABLE

| Example No. | Nature of the compound | Duration stable reaction (h) | Heavy side products (g/kg VC converted) | $[VC]_{min}$ (ppm) |
|---|---|---|---|---|
| 1 (C) | 1,1-difluoroethane | 50 | 50 | >1000 |
| 2 (C) | 1,2,3-trichloropropane | 35 | 25 | 1400 |
| 3 | 1,1,1,3,3-pentafluorobutane | 100 | 6 | 100 |
| 4 | perchloroethylene | >200 | 1 | 30 |

We claim:

1. A process for the manufacture of 1,1-difluoroethane by reaction between hydrogen fluoride and vinyl chloride in the liquid phase, wherein the reaction is carried out in a reaction medium comprising at least one compound chosen from perchloroethylene and 1,1,1,3,3-pentafluorobutane.

2. The process of claim 1, in which the said compound is perchloroethylene.

3. The process of claim 1, in which the reaction medium contains from 20 to 99.5% by weight of the said compound.

4. The process of claim 1, in which the reaction medium contains from 0.2 to 75% by weight of hydrogen fluoride.

5. The process of claim 1, in which the reaction medium contains from 0.003 to 15% by weight of vinyl chloride.

6. The process of claim 1, in which the reaction medium contains from 0.001 to 2 mol per kg of a hydrofluorination catalyst chosen from derivatives of the metals from groups IIIa, IVa, IVb, Va, Vb and VIb of the Periodic Table of the Elements.

7. The process of claim 1, in which the molar ratio between the hydrogen fluoride and the vinyl chloride used is at least 2 and does not exceed 20.

8. The process of claim 1, in which the reaction is performed at a temperature of at least 40° C. and not exceeding 130° C. and at a pressure of at least 2 bar and not exceeding 50 bar.

9. The process of claim 1, in which the 1,1,-difluoroethane is continuously withdrawn from the reaction medium.

10. The process of claim 9, in which the 1,1-difluoroethane and the hydrogen chloride produced are withdrawn in the gas phase.

11. The process of claim 1, in which at least a part of the vinyl chloride is replaced by 1,1-dichloroethane or 1-chloro-1-fluoroethane.

* * * * *